United States Patent [19]

Uno et al.

[11] Patent Number: 5,792,636
[45] Date of Patent: Aug. 11, 1998

[54] PROCESS FOR PRODUCING A STABLE CARBOXYLESTERASE IN DRY FORM

[75] Inventors: Kazutaka Uno, Tsukuba; Makoto Egi; Nobuko Egi, both of Tokyo; Nobuo Ogata, Tsuchiura, all of Japan

[73] Assignee: Kyowa Hakko Kogyo Co., Ltd., Tokyo, Japan

[21] Appl. No.: 765,913

[22] PCT Filed: Jul. 19, 1995

[86] PCT No.: PCT/JP95/01431

§ 371 Date: Jan. 14, 1997

§ 102(e) Date: Jan. 14, 1997

[87] PCT Pub. No.: WO96/02631

PCT Pub. Date: Feb. 1, 1996

[30] Foreign Application Priority Data

Jul. 20, 1994 [JP] Japan ................. 6-167806

[51] Int. Cl.⁶ ................. C12N 9/96; C12N 9/18
[52] U.S. Cl. ................. 435/188; 435/197
[58] Field of Search ................. 435/188, 197

[56] References Cited

U.S. PATENT DOCUMENTS 4,904,592  2/1990  Freeman et al. ................. 435/183

OTHER PUBLICATIONS van de Beek et al. (1969) *Neth. Milk Dairy j.*, 23, "Preservation of the Enzymatic Activity of Rennin During Spray Drying and During Storage, and the Effect of Sugars and Certain Other Additives", pp. 46–54.

Back et al. (1979) *Biochemistry*, 18(23), "Increased Thermal Stability of Proteins in the Presence of Sugars and Polyols", pp. 5191–5196.

Arakawa et al. (1982) *Biochemistry*, 21(25), "Stabilization of Protein Structure by Sugars", pp. 6536–6544.

Gekko (1982) *J. Biochem.*, 91, "Calorimetric Study on Thermal Denaturation of Lysozyme in Polyol–Water Mixtures", pp. 1197–1204.

Schmid (1979) *Adv. Biochem. Eng.*, 12, "Stabilized Soluble Enzymes", pp. 42–118.

*Primary Examiner*—Jon P. Weber
*Attorney, Agent, or Firm*—Antonelli, Terry, Stout & Kraus, LLP

[57] ABSTRACT

A process is presented for producing a stable carboxylesterase in dry form wherein a saccharide selected from maltose, maltotriose, maltotetrose, maltopentaose, maltohexaose, maltoheptaose and maltitol is added to the solution of carboxylesterase to be spray dried. The dry enzyme composition is added to food and drink (e.g., bread, brewed seasonings, liquors, processed meat products) during the production process to thereby impart thereto a good aroma (ester aromas).

3 Claims, No Drawings

PROCESS FOR PRODUCING A STABLE CARBOXYLESTERASE IN DRY FORM

TECHNICAL FIELD

The present invention relates to a process for producing a stable carboxylesterase in dry form. The dry enzyme composition is added to food and drink (e.g., bread, brewed seasonings, liquors, processed meat products) during the production process to thereby impart thereto a good aroma (ester aromas).

BACKGROUND ART

Heretofore, various substances are used in order to stabilize enzymes. For example, known are saccharides (e.g., lactose, glucose, saccharose, dextrin, arabitol, sorbitol, mannitol, inositol, β-cyclodextrin), amino acids and chelating agents (Japanese Published Unexamined Patent Application No. 34001/80) as stabilizers for sarcosine oxidase; lactose, sucrose, gelatin, aspartic acid and glutamic acid (Japanese Published Unexamined Patent Application No. 134,991/83) as stabilizer for serratiopeptidase; and sucrose, glucose, glycerol, gelatin, albumin, amino acids, etc. ("Freeze-Drying, and Protecting Substances" edited by Tokio Nei, published by Tokyo University Publishing Co., Mar. 20, 1972), and also ethylene glycol, glycerol, sorbitol, inositol, glucose, sucrose, etc. [Protein Nucleic Acid Enzyme, 30, 10, 1115 (1985)] as substances for protecting enzyme proteins.

As a laboratory reagent grade carboxylesterase (EC. 3.1.1.1), known is a carboxylesterase in liquid form derived from porcine liver such as Esterase[Product Number E3128; Catalogue from Sigma Co. (1993)] and Esterase[Product Number 104698; Catalogue from Boehringer Mannheim Co. (1991)].

Additionally known is a freeze-dried product of rabbit liver-derived carboxylesterase, Esterase [Product Number E0887; Catalogue from Sigma Co. (1993)] which is not satisfactorily stable. The analysis of this freeze-dried enzyme as carried out in accordance with the method described in "Chemistry of Saccharides (last volume), p. 329, published by Tokyo Kagaku Dojin" has revealed that any stabilizer including saccharides is not added thereto.

Carboxylesterases derived from animal organs are known not only in the laboratory use but also for industrial use, which is used only in liquid form(see WO93/09681).

DISCLOSURE OF THE INVENTION

The present invention relates to a process for producing a stable carboxylesterase in dry form, which comprises adding a saccharide to a solution containing carboxylesterase and drying the solution.

Carboxylesterase to be used in the present invention may be derived from animal organs, especially porcine, bovine, ovine or caprine organs such as liver, kidney and heart.

One embodiment of the process of the present invention for producing a stable carboxylesterase in dry form from any of such animal organs is as follows:

After an animal organ is minced, a buffer (pH 6 to 7) containing sucrose is added to the minced organ and the minced organ is shattered and then centrifuged. The resulting supernatant is adjusted to have a pH of 4.5 to 5.5 with an acid (e.g., acetic acid) and then again centrifuged to obtain a precipitate. This precipitate is defatted with a solvent (e.g., acetone) and suspended in a buffer (pH 6 to 7). Ammonium sulfate is added to the resulting suspension at 70% saturation, and centrifuged. The resulting precipitate is suspended in 3.2 M ammonium sulfate to obtain an enzyme suspension. A saccharide is added to this enzyme suspension directly thereto or after the enzyme suspension has been diluted with, for example, water or the like or after it has been dissolved through desalting. Thus is prepared a solution of the enzyme, which is then dried.

The saccharide to be added to the enzyme liquid may be at least one selected from maltose, maltotriose, maltotetraose, maltopentaose, maltohexaose, glucose, sucrose, trehalose, lactose, fructose, maltoheptaose, maltitol, maltotriitol, maltotetraitol, inositol, sorbitol and lactitol, preferably at least one selected from maltose, sucrose, maltotriose, maltotetraose, maltopentaose, maltohexaose, maltoheptaose, maltitol, maltotriitol, maltotetraitol and lactitol, more preferably maltose or maltitol.

The amount of the saccharide to be added may be 0.1 to 30% w/v, preferably 0.1 to 20% w/v, relative to the enzyme solution.

The drying may be conducted according to any of vacuum freeze-drying, spray-drying, aeration-drying or the like. The vacuum freeze-drying may be conducted at a vacuum degree of 130 Pa or lower, at a freezing temperature of −30° to −10° C., and at a shelf temperature of 5° to 40° C. The spray-drying may be conducted at an inlet temperature of 100° to 150° C. and at an outlet temperature of 50° to 120° C. The aeration-drying may be conducted at a temperature of 40° to 80° C. for 1 to 10 hours.

To prevent the enzymatic activity from being lowered during the drying process, the drying is preferably conducted under relatively mild conditions, for example, according to the vacuum freeze-drying. If desired, a vehicle can be added to the enzyme solution during the drying process. As the vehicle, dextrin or a similar compound may be employed.

The enzymatic activity of the dry carboxylesterase thus obtained is highly stable.

BEST MODE FOR CARRYING OUT THE INVENTION

Examples and Reference Examples are described below.

EXAMPLE 1

Maltose, a stabilizing substance, was dissolved in the carboxylesterase-containing solution as obtained in Reference Example 7 (having a protein concentration of 3.5 mg/ml and an activity of 180 U/ml), at a maltose concentration of 1% (w/v). The resulting solution was frozen at −20° C. for 2 hours, and then dried using a Kyowa-type freeze-drier RL-30NB Model, at a shelf temperature of 30° C. and at a vacuum degree of 13.3 Pa or lower for about 18 hours to obtain a powder enzyme composition.

The enzymatic activity of this dried enzyme composition was measured[*1], and the residual activity (%) of the enzyme thereof obtained according to the following equation[*2] was 86%.

[*1] The enzymatic activity was measured according to "Methods in Enzymology, 77, 333 (1981)", as follows: First, to prepare a substrate, 18.1 mg of p-nitrophenyl acetate was dissolved in 1 ml of acetonitrile, to which was added tris-maleate buffer (50 mM, pH 7.0) to be 100 ml in total. The substrate thus prepared was used herein. The substrate (1.8 ml) was added to 0.2 ml of a solution of the dry enzyme composition (as prepared by dissolving the composition in water), and reacted at 30°

C. for 10 minutes, to which was added 2 ml of acetone to stop the reaction. The absorbance at 405 nm of the reaction mixture was measured. The substrate prepared was used herein within 1 hour. The data verified the linearity between the amount of the enzyme used and the absorbance found, at OD of 0.2 to 1.0. Based on the molecular extinction coefficient of p-nitrophenol, 16400/M.cm, one unit was defined to be the amount of the enzyme that decomposed 1 μmol of the substrate for 1 minute under the condition employed herein.

From the data found, the residual activity (%) of the enzyme was represented by the ratio of the relative activity of the dried enzyme to that of the non-dried one, as in the following equation, the activity of the non-dried enzyme per the unit protein being 100.

*2 Residual activity (%)=[(relative activity of dried enzyme, unit/mg protein)/(relative activity of non-dried enzyme, unit/mg protein)]×100

As the control, a powder enzyme sample was prepared in the same manner as in Example 1 except that the stabilizing substance maltose was not used. The residual activity (%) of this control sample obtained in the same manner as in Example 1 was 16%.

Both powder enzyme samples of Example 1 and the control were stored at 37° C. and at a relative humidity of 65%. After 30 days, 60 days and 90 days, the residual activity (%) was obtained. The data obtained are shown in Table 1 along with those previously obtained immediately after the freeze-drying (FD). Examples 2 to 17, and Reference Examples 1 to 5:

Powder enzyme compositions were obtained in the same manner as in Example 1, except that any of the stabilizers shown in Table 1 was used in place of maltose.

The residual activity (%) of each of these samples was obtained immediately after the freeze-drying and after 30 days, 60 days and 90 days, as in Example 1. The data obtained are shown in Table 1.

TABLE 1

| Example or Reference Example | Stabilizer | Residual activity (%) | | | |
|---|---|---|---|---|---|
| | | Just After FD | After 30 days | After 60 days | After 90 days |
| Example 1 | Maltose | 86 | 82 | 88 | 82 |
| Example 2 | Sucrose | 93 | 78 | 69 | 71 |
| Example 3 | Glucose | 98 | 77 | 64 | 61 |
| Example 4 | Trehalose | 93 | 81 | 39 | 48 |
| Example 5 | Lactose | 94 | 63 | 42 | 42 |
| Example 6 | Fructose | 99 | 74 | 70 | 65 |
| Example 7 | Maltotrose | 90 | 80 | 89 | 79 |
| Example 8 | Maltotetraose | 92 | 79 | 79 | 78 |
| Example 9 | Malto-pentaose | 90 | 77 | 75 | 74 |
| Example 10 | Maltohexaose | 94 | 82 | 77 | 74 |
| Example 11 | Malto-heptaose | 93 | 82 | 75 | 73 |
| Example 12 | Maltitol | 98 | 89 | 82 | 82 |
| Example 13 | Maltotriitol | 83 | 88 | 82 | 79 |
| Example 14 | Maltotetraitol | 92 | 84 | 82 | 78 |
| Example 15 | Lactitol | 85 | 83 | 75 | 72 |
| Example 16 | Sorbitol | 66 | 54 | 52 | 46 |
| Example 17 | Inositol | 97 | 72 | 58 | 47 |
| Reference Example 1 | Cellobiose | 94 | 58 | 28 | 35 |
| Reference Example 2 | Xylose | 97 | 19 | 2 | 1 |
| Reference Example 3 | Mannitol | 65 | 52 | 27 | 24 |
| Reference Example 4 | Xylitol | 41 | 32 | 18 | 15 |

TABLE 1-continued

| Example or Reference Example | Stabilizer | Residual activity (%) | | | |
|---|---|---|---|---|---|
| | | Just After FD | After 30 days | After 60 days | After 90 days |
| Reference Example 5 | Erythritol | 21 | 9 | 4 | 3 |
| Control | Not Added | 16 | 3 | 0 | 0 |

As is obvious from the data in the table above, the stability of the powder enzyme samples of Examples after storage over a long period of time is much higher not only than that of the control sample but also than that of the powder enzyme samples of Reference Examples.

EXAMPLE 18

Powder enzyme compositions were obtained in the same manner as in Example 1, except that maltitol was used in place of maltose and the maltitol concentration (% w/v) was varied to 0.02, 0.1, 1, 5, 10, 20, 30 and 40. The residual activity (%) of each of these samples was obtained in the same manner as in Example 1. The data obtained are shown in Table 2.

TABLE 2

| Maltitol Concentration (% w/v) | Residual activity (%) | Condition of Dried Sample* |
|---|---|---|
| 0.02 | 18 | A |
| 0.1 | 98 | A |
| 1 | 98 | A |
| 5 | 100 | A |
| 10 | 92 | A |
| 20 | 100 | A |
| 30 | 95 | B |
| 40 | 95 | C |

* Condition of Dried Sample:
A: Good and dry powder
B: Somewhat wet powder
C: Viscous paste As is obvious from the data in the table above, it is understood that the concentration of maltitol to be added shall be from 0.1 to 30% w/v, preferably from 0.1 to 20% w/v.

EXAMPLE 19

Maltitol, a stabilizer, was dissolved in the carboxylesterase-containing solution as obtained in Reference Example 7 (having a protein concentration of 3.5 mg/ml and an activity of 180 U/ml), at a maltitol concentration of 1% w/v. The resulting solution was spray-dried using a spray-drier (SD-1 Model, produced by Tokyo Rika Kiki Co.), at an inlet temperature of 105° C. and at an outlet temperature of 70° C. The residual activity (%) of the powder enzyme composition thus obtained was measured in the same manner as in Example 1 to be 71%.

REFERENCE EXAMPLE 6

A powder enzyme sample was obtained in the same manner as in Example 19, except that maltitol, the stabilizer, was not used. The residual activity (%) of this sample obtained in the same manner as in Example 1 was 20%.

EXAMPLES 20 TO 23

Maltose, a stabilizer, was dissolved in any of the porcine kidney-derived, bovine liver-derived, bovine kidney-derived or bovine heart-derived carboxylesterase-containing solution as obtained in any of Reference Examples 8 to 11, at a maltose concentration of 1% w/v. Each solution was frozen at −20° C. for 2 hours, and then dried, using a Kyowa-type freeze-drier RL-30NB Model, at a shelf temperature of 30° C. and at a vacuum degree of 13.3 Pa or lower for about 18 hours to obtain a powder enzyme composition. The residual activity (%) of each sample obtained herein was obtained in the same manner as in Example 1. The data obtained are shown in Table 3.

TABLE 3

| Example | Source of Enzyme | Residual activity (%) |
| --- | --- | --- |
| 20 | Porcine Kidney | 92 |
| 21 | Bovine Liver | 91 |
| 22 | Bovine Kidney | 89 |
| 23 | Bovine Heart | 90 |

REFERENCE EXAMPLE 7

After 1 kg of porcine liver was minced, 3000 ml of 0.02 M phosphate buffer (pH 6.5) containing 0.25% w/v sucrose was added to the minced liver and the minced liver was shattered and then centrifuged (10000 ×g, 30 minutes). The resulting supernatant was adjusted to have a pH of 5.3 with 2 N acetic acid, then left at 4° C. for 10 hours, and then again centrifuged (10000 ×g, 30 minutes) to obtain a precipitate. Then, 1000 ml of cold acetone (−20° C.) was added thereto, stirred and then filtered under suction through Toyo Filter Paper No. 2. This defatting with acetone was repeated three times, and the resulting residue was dried in a vacuum drier at 20° C. to remove the remaining acetone. To the residue thus dried was added 1000 ml of 0.05 M phosphate buffer (pH 6.7), stirred at 4° C. for 10 hours, and centrifuged (10000 ×g, 30 minutes) to obtain a supernatant. Ammonium sulfate was added to the resulting supernatant at 50% saturation, left at 4° C. for 5 hours, and centrifuged (10000 ×g, 30 minutes) to remove the precipitate. Ammonium sulfate was added to the resulting supernatant at 70% saturation, left at 4° C. for 5 hours, and centrifuged (10000 ×g, 30 minutes). To the precipitate thus obtained was added 3.2 M ammonium sulfate to make 100 ml in total. Thus was obtained a porcine liver-derived enzyme solution.

REFERENCE EXAMPLES 8 TO 11

Various animal organ-derived enzyme solutions were obtained in the same manner as in Reference Example 7, except that a porcine kidney, a bovine liver, a bovine kidney or bovine heart was used in place of the porcine kidney.

According to the present invention, a stable carboxylesterase in dry form is provided.

INDUSTRIAL APPLICABILITY

According to the present invention, a stable carboxylesterase in dry form is provided. The dry enzyme composition is added to food and drink (e.g., bread, brewed seasonings, liquors, processed meat products) during the production process to thereby impart thereto a good aroma (ester aromas).

We claim:

1. A process for producing a stable carboxylesterase in dry form, which comprises adding a saccharide to a solution containing carboxylesterase and drying the solution, wherein the saccharide is at least one selected from maltose, maltotriose, maltotetraose, maltopentaose, maltohexaose, maltoheptaose and maltitol.

2. The process for producing a stable carboxylesterase in dry form according to claim 1, wherein the saccharide is maltose or maltitol.

3. The process according to claim 1, wherein the saccharide is at least one selected from maltotriose, maltotetraose, maltopentaose, maltohexaose, maltoheptaose and maltitol.

* * * * *